(12) United States Patent
Burkhard

(10) Patent No.: US 8,575,110 B2
(45) Date of Patent: Nov. 5, 2013

(54) PEPTIDIC NANOPARTICLES AS DRUG DELIVERY AND ANTIGEN DISPLAY SYSTEMS

(75) Inventor: Peter Burkhard, Basel (CH)

(73) Assignee: Alpha-O Peptides G, Riehen (CH)

( * ) Notice: Subject to any disclaimer, the term of this patent is extended or adjusted under 35 U.S.C. 154(b) by 1677 days.

(21) Appl. No.: 10/545,676

(22) PCT Filed: Feb. 16, 2004

(86) PCT No.: PCT/IB2004/000423
§ 371 (c)(1),
(2), (4) Date: Aug. 15, 2005

(87) PCT Pub. No.: WO2004/071493
PCT Pub. Date: Aug. 26, 2004

(65) Prior Publication Data
US 2007/0014804 A1    Jan. 18, 2007

(30) Foreign Application Priority Data
Feb. 17, 2003  (EP) .................................... 03003551

(51) Int. Cl.
A61K 38/00   (2006.01)
A61K 39/00   (2006.01)
C07K 14/00   (2006.01)
C07K 2/00    (2006.01)

(52) U.S. Cl.
USPC ........ 514/21.3; 514/1.1; 424/184.1; 530/300; 530/350

(58) Field of Classification Search
None
See application file for complete search history.

(56) References Cited

U.S. PATENT DOCUMENTS

| 5,008,373 | A | * | 4/1991 | Kingsman et al. | 530/350 |
| 5,877,279 | A | * | 3/1999 | Goldberg | 530/350 |
| 6,756,039 | B1 | | 6/2004 | Yeates et al. | |
| 2003/0092069 | A1 | | 5/2003 | Kuroda et al. | |

FOREIGN PATENT DOCUMENTS

| EP | 0 201 416 | | 11/1986 |
| EP | 1 262 555 | | 12/2002 |
| WO | WO 00/68248 | * | 11/2000 |

OTHER PUBLICATIONS

GenBank No. NP_000086 of COMP sequence, pp. 1-3. Accessed on Aug. 28, 2008.*
Definition of pentamer from http://medical-dictionary.thefreedictionary.com/pentameric, pp. 1-2. Accessed Mar. 27, 2009.*
Definition of derivative from http://cancerweb.ncl.ac.uk/cgi-bin/omd?query=analog, pp. 1-5. Accessed Jul. 7, 2005.*
Oldberg A, Antonsson P, Lindblom K, Heinegard D, "COMP (Cartilage Oligomeric Matrix Protein) is Structurally Related to the Thrombospondins," The Journal of Biological Chemistry, 1992, 267(31): 22346-22350.*
Gill SR, Schroer TA, Szilak I, Steuer ER, Sheetz MP, Cleveland DW, "Dynactin, a conserved, ubiquitously expressed component of an activator of vesicle motility mediated by cytoplasmic dynein," Journal of Cell Biology, 1991, 115(6): 1639-1650.*
Paul Pumpens et al., "Hepatitis B core particles as a universal display model: a structure-function basis for development", FEBS Letters, vol. 442, No. 1, pp. 1-6, 1999, XP002937462.
Peter Burkhard et al., "Coiled coils: a highly versatile protein folding motif", Trends in Cell Biology, vol. 11, No. 2, pp. 82-88, Feb. 2001, XP002255516.
Markus Meier et al., "Removing an Interhelical Salt Bridge Abolishes Coiled-Coil Formation in a de Novo Designed Peptide", Journal of Structural Biology, vol. 137., No. 1, pp. 65-72, XP002255517, 2002.
Jennifer E. Padilla et al., "Nanohedra: Using symmetry to design self assembling protein cages, layers, crystals, and filaments", PNAS, vol. 98, No. 5, pp. 2217-2221, Feb. 27, 2001.
Todd O. Yeates, et al., "Designing supramolecular protein assemblies", Current Opinion in Structural Biology, 12, pp. 464-470, 2002.

* cited by examiner

*Primary Examiner* — Julie Ha
(74) *Attorney, Agent, or Firm* — Wenderoth, Lind & Ponack, L.L.P.

(57) ABSTRACT

Described is a new type of nanoparticle using the concept of self-organization of a single continuous chain to form peptidic nanoparticles. In particular, nanoparticles of the invention consist of aggregates of a continuous chain comprising two peptidic oligomerization domains connected by a linker segment. Preferred are coiled-coil oligomerization domains with a contiguous pattern of hydrophobic residues spaced 3 and 4 residues apart. The invention provides a drug targeting and delivery system comprising a functionalized peptidic nanoparticle comprising ligands capable of binding a receptor and drugs, and a method of treating or diagnosing humans using such functionalized peptidic nanoparticles. The invention further provides an antigen display system to be used as efficient vaccines comprising a functionalized peptidic nanoparticle comprising an antigen, and a method of vaccinating humans or non-human animals using such functionalized peptidic nanoparticles. The invention also provides processes for making peptidic nanoparticles and functionalized peptidic nanoparticles, and monomeric building blocks suitable for forming such nanoparticles.

11 Claims, 4 Drawing Sheets

A)    B)

```
SEQUENCE LISTING

<160> NUMBER OF SEQ ID NOS: 8

<210> SEQ ID NO 1
<211> LENGTH: 64
<212> TYPE: PRT
<213> ORGANISM: Artificial
<220> FEATURE:
<223> OTHER INFORMATION: Synthetic Construct

<400> SEQUENCE: 1

Asp Glu Met Leu Arg Glu Leu Gln Glu Thr Asn Ala Ala Leu Gln Asp
1               5                   10                  15

Val Arg Glu Leu Leu Arg Gln Gln Val Lys Gln Ile Thr Phe Leu Lys
            20                  25                  30

Cys Leu Leu Met Gly Gly Arg Leu Leu Cys Arg Leu Glu Leu Leu Glu
        35                  40                  45

Arg Arg Leu Glu Glu Leu Glu Arg Arg Leu Glu Glu Leu Glu Arg Arg
    50                  55                  60

<210> SEQ ID NO 2
<211> LENGTH: 66
<212> TYPE: PRT
<213> ORGANISM: Artificial
<220> FEATURE:
<223> OTHER INFORMATION: Synthetic Construct

<400> SEQUENCE: 2

Gly Ser Asp Glu Met Leu Arg Glu Leu Gln Glu Thr Asn Ala Ala Leu
```

```
            1               5                   10                  15
Gln Asp Val Arg Glu Leu Leu Arg Gln Gln Val Lys Gln Ile Arg Arg
            20                  25                  30

Leu Lys Arg Leu Leu Arg Gly Gly Arg Leu Leu Ala Glu Leu Glu Glu
            35                  40                  45

Leu Arg Glu Arg Leu Glu Gln Leu Glu Arg Arg Leu Glu Glu Leu Glu
            50                  55                  60

Arg Arg
65

<210> SEQ ID NO 3
<211> LENGTH: 75
<212> TYPE: PRT
<213> ORGANISM: Artificial
<220> FEATURE:
<223> OTHER INFORMATION: Synthetic Construct

<400> SEQUENCE: 3

Gly Ser Gly Tyr Ile Pro Glu Ala Pro Arg Asp Gly Gln Ala Tyr Val
1               5                   10                  15

Arg Lys Asp Gly Glu Trp Val Leu Leu Ser Thr Phe Leu Gly Gly Leu
            20                  25                  30

Ala Pro Gln Met Leu Arg Glu Leu Gln Glu Thr Asn Ala Ala Leu Gln
            35                  40                  45

Asp Val Arg Glu Leu Leu Arg Gln Gln Val Lys Gln Ile Thr Phe Leu
            50                  55                  60

Lys Asn Thr Val Met Glu Cys Asp Ala Cys Gly
65                  70                  75

<210> SEQ ID NO 4
<211> LENGTH: 75
<212> TYPE: PRT
<213> ORGANISM: Artificial
<220> FEATURE:
<223> OTHER INFORMATION: Synthetic Construct

<400> SEQUENCE: 4

Gly Ser Gly Tyr Ile Pro Glu Ala Pro Arg Cys Gly Gln Ala Tyr Val
1               5                   10                  15

Arg Lys Asp Gly Glu Trp Val Leu Leu Ser Thr Phe Leu Gly Gly Leu
            20                  25                  30

Ala Pro Gln Met Leu Arg Glu Leu Gln Glu Thr Asn Ala Ala Leu Gln
            35                  40                  45

Asp Val Arg Glu Leu Leu Arg Gln Gln Val Lys Gln Ile Thr Phe Leu
            50                  55                  60

Lys Asn Thr Val Met Glu Cys Asp Ala Cys Gly
65                  70                  75

<210> SEQ ID NO 5
<211> LENGTH: 77
<212> TYPE: PRT
<213> ORGANISM: Artificial
<220> FEATURE:
<223> OTHER INFORMATION: Synthetic Construct

<400> SEQUENCE: 5

Gly Ser Gly Tyr Ile Pro Glu Ala Pro Arg Cys Gly Gln Ala Tyr Val
1               5                   10                  15

Arg Lys Asp Gly Glu Trp Val Leu Leu Ser Thr Phe Leu Gly Gly Ser
            20                  25                  30
```

```
Gly Leu Ala Pro Gln Met Leu Arg Glu Leu Gln Glu Thr Asn Ala Ala
            35                  40                  45

Leu Gln Asp Val Arg Glu Leu Leu Arg Gln Gln Val Lys Gln Ile Thr
        50                  55                  60

Phe Leu Lys Asn Thr Val Met Glu Cys Asp Ala Cys Gly
65                  70                  75

<210> SEQ ID NO 6
<211> LENGTH: 79
<212> TYPE: PRT
<213> ORGANISM: Artificial
<220> FEATURE:
<223> OTHER INFORMATION: Synthetic Construct

<400> SEQUENCE: 6

Gly Ser Gly Tyr Ile Pro Glu Ala Pro Arg Cys Gly Gln Ala Tyr Val
1               5                   10                  15

Arg Lys Asp Gly Glu Trp Val Leu Leu Ser Thr Phe Leu Gly Gly Ser
            20                  25                  30

Gly Ser Gly Leu Ala Pro Gln Met Leu Arg Glu Leu Gln Glu Thr Asn
        35                  40                  45

Ala Ala Leu Gln Asp Val Arg Glu Leu Leu Arg Gln Gln Val Lys Gln
    50                  55                  60

Ile Thr Phe Leu Lys Asn Thr Val Met Glu Cys Asp Ala Cys Gly
65                  70                  75

<210> SEQ ID NO 7
<211> LENGTH: 44
<212> TYPE: PRT
<213> ORGANISM: Rattus norvegicus

<400> SEQUENCE: 7

Leu Ala Pro Gln Met Leu Arg Glu Leu Gln Glu Thr Asn Ala Ala Leu
1               5                   10                  15

Gln Asp Val Arg Glu Leu Leu Arg Gln Gln Val Lys Gln Ile Thr Phe
            20                  25                  30

Leu Lys Asn Thr Val Met Glu Cys Asp Ala Cys Gly
        35                  40

<210> SEQ ID NO 8
<211> LENGTH: 27
<212> TYPE: PRT
<213> ORGANISM: Bacteriophage T4

<400> SEQUENCE: 8

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25
```

PEPTIDIC NANOPARTICLES AS DRUG DELIVERY AND ANTIGEN DISPLAY SYSTEMS

FIELD OF THE INVENTION

The present invention relates to nanoparticles. Furthermore, the invention relates to the targeting of drugs to particular body locations, to antigen display systems and to vaccination strategies.

BACKGROUND OF THE INVENTION

Artificial particulate systems such as polymeric beads and liposomes are finding a variety of biomedical applications in drug delivery, drug targeting, protein separation, enzyme immobilization and blood cell substitution. Liposomes have a flexible, cell-like lipid bilayer surface which acts as a permeability barrier such that compounds can be entrapped in their aqueous interior. However, liposomes can be mechanically unstable and their loading capacity limited by the water solubility of the material to be loaded. Other approaches for the preparation of nanometer- to micrometer-sized spherical polymer shells involve the layer-by-layer deposition of polyelectrolytes on the surface of a charged nanoparticle followed by the dissolution of the templating particle or the self assembly of amphiphilic diblock copolymers into micelles, selective cross-linking of their hydrophilic shell, and subsequent degradation of the hydrophobic core. Preparation of such nanocapsules requires a rather complex process. Also, polymeric beads, although mechanically more stable and having a larger loading capacity than liposomes, lack many of the useful surface properties of a lipid bilayer shell.

Drug targeting systems have been described in various patent publications and scientific articles. Specific antibodies carrying diagnostic or therapeutic agents targeted to the site of action displaying the corresponding antigen are widely used (Vyas S. P. et al., Crit Rev Ther Carrier Syst 2001, 18(1):1-76).

Nanoparticles have been studied extensively as particulate carriers in several pharmaceutical and medical fields (Sakuma S. et al., Adv Drug Del Rev 2001, 47:21-37). It is well known that the bioavailability of peptide and protein drugs after oral administration is very low because of their instability in the gastrointestinal (GI) tract and low permeability through the intestinal mucosa. Therefore, injectable dosage forms are currently used to obtain therapeutic effects. However, since these administration routes are poorly accepted by patients, it is indispensable to develop alternatives such as nasal, buccal, rectal, vaginal, pulmonary and transdermal routes. Oral administration is the most convenient route for drug delivery, and several approaches such as chemical modification to alter the physicochemical properties of peptide drugs, the use of an absorption enhancer to promote drug absorption and the use of a protease inhibitor to protect drugs against degradation by enzymes have been investigated in Order to achieve oral peptide delivery. Nanoparticles have been studied as carriers for oral drug delivery. The aims of the studies done on nanoparticles as oral drug carriers were improvement of the bioavailability of drugs with poor absorption characteristics, delivery of vaccine antigens to the gut-associated lymphoid tissues, control of the release of drugs, reduction of the GI mucosa irritation caused by drugs, and assurance of the stability of drugs in the GI tract.

Also circulation times in the blood can be modified by particulate administration of drugs. The need for recirculation of therapeutic agents in the body, that is avoidance of rapid endocytosis by the reticuloendothelial system and avoidance of rapid filtration by the kidney, to provide sufficient concentration at a targeted site to afford necessary therapeutic effect has been recognized. Small molecules, such as gadolinium diethylenetriaminepentaacetic acid, tend to have limited circulation times due to rapid renal excretion while most liposomes, having diameters greater than 800 nm, are quickly cleared by the reticuloendothelial system.

The traditional immunization arsenal includes vaccines that use live attenuated organisms, inactivated organisms, conventional whole proteins, and, more recently, naked DNA. From an immunological standpoint, based on the broad range of humoural and cellular immune responses generated and the memory responses they induce, live attenuated vaccines still represent the vaccines of choice (BenMohammed L. et al., Lancet Infect Dis 2002, 2:425-431). From a practical and safety standpoint, however, live attenuated vaccines raise issues related to manufacturing and safety that may preclude their widespread use. As an alternative, peptide-based vaccines have now been developed and used for vaccination. Peptide-based vaccines offer several potential advantages over the conventional whole proteins (or whole gene, in the case of genetic immunization) in terms of purity and a high specificity in eliciting immune responses. However, synthetic peptides alone are often not immunogenic enough, and a strong immunoadjuvant is usually employed for their elaboration. Concerns about toxic adjuvants, however, which are critical for immunogenicity of synthetic peptides, still remain. And maybe even more critical is the problem of human genetic heterogeneity, which results in varying strength of immune responses.

One potential solution for stabilizing peptide-based vaccines is the presentation of epitopes embedded in a coiled-coil peptide composition as described in WO 01/00010. Viral particles, in particular particles formed from hepatitis virus B surface antigens, have been considered as nanoparticles useful for antigen presentation (EP 201 416) or for the transport of substances into target cells and tissue (EP 1262 555).

There is a need for improved types of mechanically and chemically stable vesicles and nanocapsules to be used for drug targeting and antigen presentation.

SUMMARY OF THE INVENTION

It is an object of the present invention to provide a new type of nanoparticle, using the concept of self-organization of continuous peptidic chains to form peptidic nanoparticles. In particular, nanoparticles of the invention consist of aggregates of a continuous peptidic chain comprising two oligomerization domains connected by a linker segment.

It is a further object of the present invention to provide a drug targeting and delivery system comprising a functionalized peptidic nanoparticle, which consists of aggregates of a continuous peptidic chain having a ligand attached to it capable of binding a receptor, and a drug attached to said peptidic chain.

It is a further object of the present invention to provide a therapeutic method of treating humans having diseased organs or tissues using such functionalized peptidic nanoparticles, and a diagnostic method for determining whether a human has diseased organs or tissues using such functionalized peptidic nanoparticles.

It is a further object of the present invention to provide an antigen display system to be used as efficient vaccines comprising a functionalized peptidic nanoparticle, which consists of aggregates of a continuous peptidic chain comprising an antigen attached to it or incorporated into it, and a method of vaccinating humans or non-human animals using such functionalized peptidic nanoparticles.

The invention also provides processes for making peptidic nanoparticles and functionalized peptidic nanoparticles of the invention, and monomeric building blocks suitable for forming nanoparticles of the invention.

DETAILED DESCRIPTION OF THE INVENTION

Figure 1:
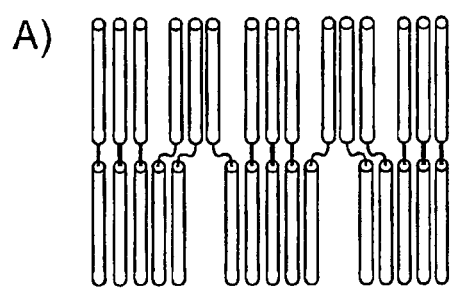
FIG. 1: Schematic drawing of "even units" for trimeric and pentameric oligomerization domains [left side, A)] and trimeric and tetrameric oligomerization domains [right side, B)], respectively. The number of monomers (building blocks) is defined by the least common multiple (LCM) of the oligomerization states of the two oligomerization domains D1 and D2 of the building blocks. In the even units the linker segments of all building blocks will be arranged as closely to each other as possible, i.e. as close to the center of the peptidic nanoparticle as possible and hence the even units will form a spherical peptidic nanoparticle.
Figure 1:
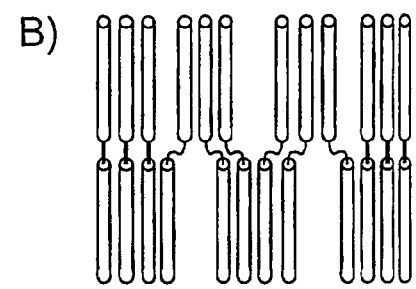
Figure 2:
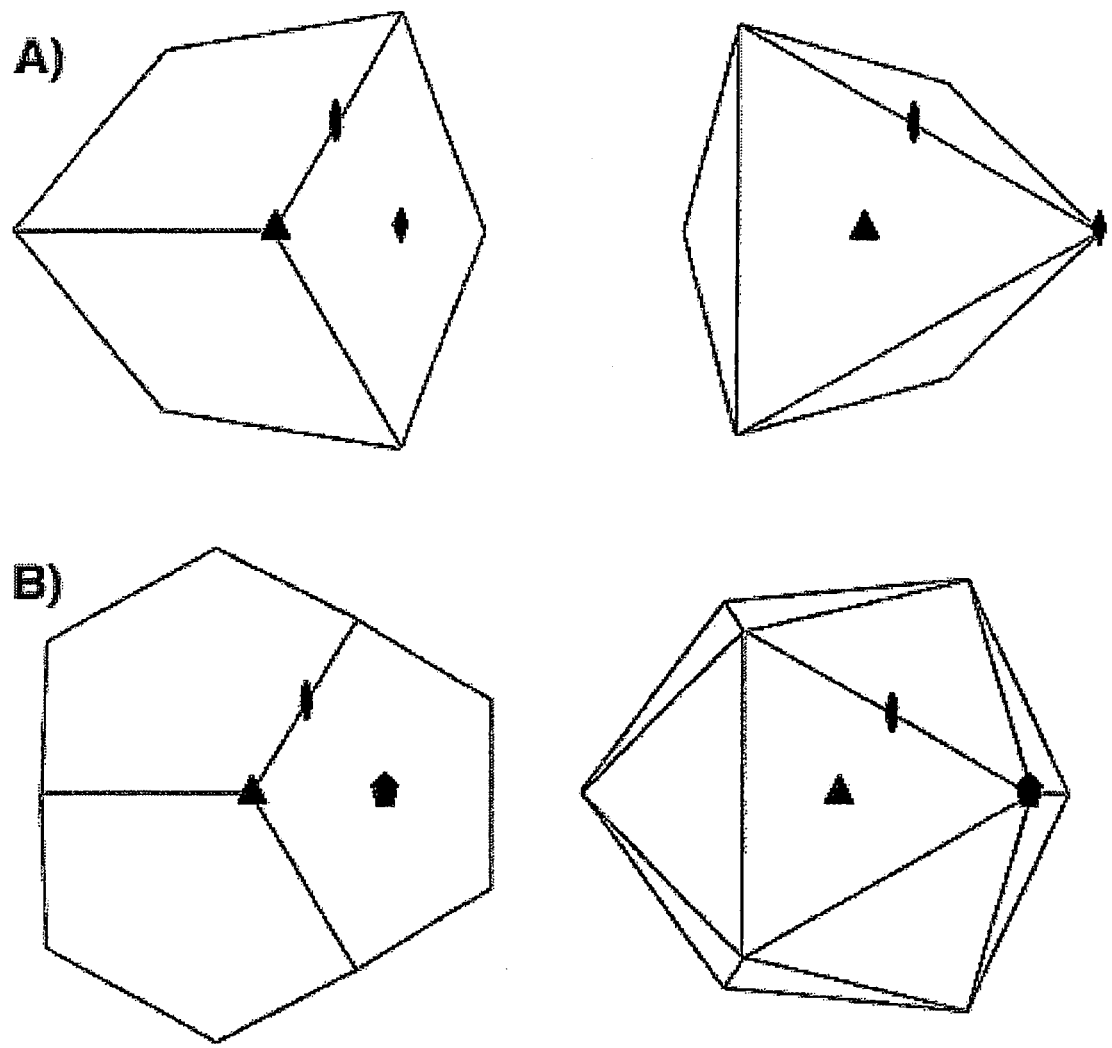
FIG. 2: Possible regular polyhedra built up from 2, 3 and 4-fold symmetry elements (A) and from 2, 3, and 5-fold symmetry elements (B). The symmetry elements are denoted as black symbols. In A) the cube (left) and the octahedron (right) have the same symmetry elements, and are built up from 24 identical three-dimensional building blocks. In B) the dodecahedron and the icosahedron have also the same internal symmetry elements and are built up from 60 identical three-dimensional building blocks.

Peptidic nanoparticles, methods of producing peptidic nanoparticles and use of these peptidic nanoparticles in diagnosis and therapy, in accordance with the invention will now be described, by way of example only, with reference to the accompanying FIGS. 1 to 4.

Peptidic Nanoparticles
Monomeric Building Blocks

Peptidic nanoparticles are formed from a multitude of monomeric building blocks of formula (I) consisting of a continuous chain comprising a peptidic oligomerization domain D1, a linker segment L and a peptidic oligomerization domain D2

$$D1\text{-}L\text{-}D2 \qquad (I),$$

wherein D1 is a synthetic or natural peptide having a tendency to form oligomers $(D1)_m$ of m subunits D1, D2 is a synthetic or natural peptide having a tendency to form oligomers $(D2)_n$ of n subunits D2, m and n each is a figure between 2 and 10, with the proviso that m is not equal n and not a multiple of n, and n is not a multiple of m, L is a bond or a short linker chain selected from optionally substituted carbon atoms, optionally substituted nitrogen atoms, oxygen atoms and sulfur atoms; and wherein D1, D2 and L are optionally further substituted.

A peptide (or polypeptide) is a chain or sequence of amino acids covalently linked by amide bonds. The term amino acid embraces both naturally occurring amino acids selected from the 20 essential natural α-L-amino acids, synthetic amino acids, such as α-D-amino acids, 6-aminohexanoic acid, norleucine, homocysteine, or the like, as well as naturally-occurring amino acids which have been modified in some way to alter certain properties such as charge, such as phoshoserine or phosphotyrosine, or the like. In derivatives of amino acids the amino group forming the amide bond is alkylated, or a side chain amino, hydroxy or thio functions is alkylated or acylated, or a side chain carboxy function is amidated or esterified.

A short linker chain L is selected from optionally substituted carbon atoms, optionally substituted nitrogen atoms, oxygen atoms and sulfur atoms, with preferably 1 to 60 atoms, in particular 1 to 20 atoms in the chain. Such a short linker chain is, e.g. an polyethyeleneoxy chain, a sugar chain or, preferably, a peptide chain, e.g. a peptide chain consisting of 1 to 20 amino acids, in particular 1 to 6 amino acids.

Optional substituents of D1, D2 and L are e.g. targeting entities, drugs and antigens as described hereinbelow.

A tendency to form oligomers means that such peptides can form oligomers depending on the conditions, e.g. under denaturing conditions they are monomers, while under physiological conditions they may form for example trimers. Their oligomerization state may be changed upon changing conditions, e.g. from dimers to trimers upon increasing salt concentration (Burkhard P. et al., Protein Science 2000, 9:2294-2301) or from pentamers to monomers upon decreasing pH. However, under predefined conditions they adopt one single oligomerization state, which is needed for nanoparticle formation.

A building block architecture according to formula (I) is clearly distinct from viral capsid proteins. Viral capsids are composed of either one single protein, which forms oligomers of 60 or a multiple thereof, as e.g. the hepatitis virus B particles (EP 1 262 555, EP 201416), or of more than one protein, which coassemble to form the viral capsid structure, which can adopt also other geometries apart from icosahedra, depending on the type of virus (Fender P. et al., Nature Biotechnology 1997, 15:52-56). Peptidic nanoparticles of the present invention are also clearly distinct from virus-like particles, as they (a) are constructed from other than viral capsid proteins and (b) that the cavity in the middle of the nanoparticle is too small to accommodate the DNA/RNA of a whole viral genome.

Peptidic oligomerization domains are well-known (Burkhard P. et al., Trends Cell Biol 2001, 11:82-88). The most simple oligomerization domain is probably the coiled-coil folding motif. This oligomerization motif has been shown to exist as a dimer, trimer, tetramer and pentamer. Some examples are the GCN4 leucine zipper, fibritin, tetrabrachion and COMP, representing dimeric, trimeric, tetrameric and pentameric coiled coils, respectively (Burkhard P. et al., loc. cit.).

In a preferred embodiment the oligomerization domains D1 and D2, independently of each other, are coiled-coil domains. A coiled-coil is a peptide sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled-coils with sequences including some irregular distribution of the 3 and 4 residues spacing are also contemplated. Hydrophobic residues are in particular the hydrophobic amino acids Val, Ile, Leu, Met, Tyr, Phe and Trp. Mainly hydrophobic means that at least 50% of the residues must be selected from the mentioned hydrophobic amino acids.

For example, in a preferred monomeric building block of formula (I), D1 and/or D2 is a peptide of the formula

[aa(a)-aa(b)-aa(c)-aa(d)-aa(e)-aa(f)-aa(g)]x   (II), wherein aa means an amino acid or a derivative thereof, aa(a), aa(b), aa(c), aa(d), aa(e), aa(f), and aa(g) are the same or different amino acids or derivatives thereof, preferably aa(a) and aa(d) are the same or different hydrophobic amino acids or derivatives thereof; and X is a figure between 2 and 20, preferably 3, 4, 5 or 6.

Hydrophobic amino acids are Val, Ile, Leu, Met, Tyr, Phe and Trp.

A heptad is a heptapeptide of the formula aa(a)-aa(b)-aa(c)-aa(d)-aa(e)-aa(f)-aa(g).

Preferred are monomeric building blocks of formula (I) wherein one or both peptidic oligomerization domains D1 or D2 are (1) a peptide of formula (II) wherein X is 3, and aa(a) and aa(d) are selected from the 20 natural α-L-amino acids such that the sum of scores from Table 1 for these 6 amino acids is at least 14, and such peptides comprising up to 17 further heptads; or

TABLE 1

Scores of amino acid for detemination of preference

| amino acid | position aa(a) | position aa(d) |
|---|---|---|
| L (Leu) | 3.5 | 3.8 |
| M (Met) | 3.4 | 3.2 |
| I (Ile) | 3.9 | 3.0 |
| Y (Tyr) | 2.1 | 1.4 |
| F (Phe) | 3.0 | 1.2 |
| V (Val) | 4.1 | 1.1 |
| Q (Gln) | −0.1 | 0.5 |
| A (Ala) | 0.0 | 0.0 |
| W (Trp) | 0.8 | −0.1 |
| N (Asn) | 0.9 | −0.6 |
| H (His) | −1.2 | −0.8 |
| T (Thr) | 0.2 | −1.2 |
| K (Lys) | −0.4 | −1.8 |
| S (Ser) | −1.3 | −1.8 |
| D (Asp) | −2.5 | −1.8 |
| E (Glu) | −2.0 | −2.7 |
| R (Arg) | −0.8 | −2.9 |
| G (Gly) | −2.5 | −3.6 |
| P (Pro) | −3.0 | −3.0 |
| C (Cys) | 0.2 | −1.2 |

(2) a peptide of formula (II) wherein X is 3, and aa(a) and aa(d) are selected from the 20 natural α-L-amino acids such that the sum of scores from Table 1 for these 6 amino acids is at least 12, with the proviso that one amino acid aa(a) is a charged amino acid able to form an inter-helical salt bridge to an amino acid aa(d) or aa(g) of a neighboring heptad, or that one amino acid aa(d) is a charged amino acid able to form an inter-helical salt bridge to an amino acid aa(a) or aa(e) of a neighboring heptad, and such peptides comprising up to two further heptads. A charged amino acid able to form an inter-helical salt bridge to an amino acid of a neighbouring heptad is, for example, Asp or Glu if the other amino acid is Lys, Arg or His, or vice versa.

Also preferred are monomeric building blocks of formula (I) wherein one or both peptidic oligomerization domains D1 or D2 are selected from the following preferred peptides:

(11) Peptide of formula (II) wherein
aa(a) is selected from Val, Ile, Leu and Met, and a derivative thereof, and
aa(d) is selected from Leu, Met and Ile, and a derivative thereof.

(12) Peptide of formula (II) wherein one aa(a) is Asn and the other aa(a) are selected from Asn, Ile and Leu, and aa(d) is Leu. Such a peptide is usually a dimerization domain (m or n=2).

(13) Peptide of formula (II) wherein aa(a) and aa(d) are both Leu or both Ile. Such a peptide is usually a trimerization domain (m or n=3).

(14) Peptide of formula (II) wherein aa(a) is either Leu or Ile, and one aa(d) is Gln and the other aa(d) are selected from Gln, Leu and Met. Such a peptide has the potential to be a pentamerization domain (m or n=5).

Other preferred peptides are peptides (1), (2), (11), (12), (13) and (14), as defined hereinbefore, and wherein further

(21) at least one aa(g) is selected from Asp and Glu and aa(e) in a following heptad is Lys, Arg or His; and/or

(22) at least one aa(g) is selected from Lys, Arg and His, and aa(e) in a following heptad is Asp or Glu, and/or

(23) at least one aa(a to g) is selected from Lys, Arg and His, and an aa(a to g) 3 or 4 amino acids apart in the sequence is Asp or Glu. Such pairs of amino acids aa(a to g) are, for example aa(b) and aa(e) or aa(f).

In another preferred embodiment, one oligomerization domain D1 or D2 is the pentamerization domain (m or n=5) of COMP (Malashkevich V. N. et al., Science 1996, 274:761-765) or a derivative thereof. This pentamerization domain has the sequence LAPQMLRELQETNAALQDVRELLRQQVKQITFLKNTVMECDACG (SEQ ID NO:7). Small modifications of this domain are also envisaged. Such modifications may be e.g. the substitution of amino acids at the outside of the pentamer, preferably in position (f), by Cys for the purpose of the formation of a disulfide bridge between adjacent domains. Other modifications of surface amino acids of this domain may include substitutions of amino acids for optimizing the interactions at the interface between adjacent oligomerization domains such as hydrophobic, hydrophilic or ionic interactions or covalent bonds like disulfide bridges. Also shorter constructs of this domain, e.g. lacking the C-terminal CDACG motif in which the cysteins form intermolecular disulfide bridges at the C-terminus of this pentamerization domain are also envisaged. Modification of amino acids affecting the oligomerization state of this domain are also envisaged, resulting e.g. in a transition from pentamer to tetramer. Yet other modifications of surface amino acids of this domain may include substitutions of amino acids (e.g. by cysteine or lysine) for the generation of attachment sites for functional groups.

In yet another preferred embodiment, one oligomerization domain D1 or D2 is the trimerization domain (foldon) of the bacteriophage T4 protein fibritin (Tao, Y. et al., Structure 1997, 5:789-798) or a derivative thereof. This trimerization domain (m or n=3) has the sequence GYI-PEAPRDGQAYVRKDGEWVLLSTFL (SEQ ID NO:8). Small modifications of this domain are also envisaged. Such modifications may be the substitution of Asp 9 by Cys for the purpose of the formation of a disulfide bridge between adjacent domains. Other modifications of surface amino acids of this domain may include substitutions of residues for optimizing the interactions at the interface between adjacent oligomerization domains such as hydrophobic, hydrophilic or ionic interactions or covalent bonds like disulfide bridges. Yet other modifications of surface amino acids of this domain may include substitutions of amino acids (e.g. by cysteine or lysine) for the generation of attachment sites for functional groups.

Most preferred are the monomeric building blocks described in the examples.

Peptidic Nanoparticles: Even Units

Peptidic nanoparticles are formed from monomeric building blocks of formula (I). If such building blocks assemble, they will form so-called "even units". The number of monomeric building blocks, which will assemble into such an even unit will be defined by the least common multiple (LCM). Hence, if for example the oligomerization domains of the monomeric building block form a trimer $(D1)_3$ (m=3) and a pentamer $(D2)_5$ (n=5), 15 monomers will form an even unit (FIG. 1A, Example 5). If the linker segment L has the appropriate length, this even unit may assemble in the form of a spherical peptidic nanoparticle. Similarly, if the oligomerization domains D1 and D2 of the monomeric block form a trimer $(D1)_3$ (m=3) and a tetramer $(D2)_4$ (n=4), the number of monomers needed to form an even unit will be 12 (FIG. 1B).

Since m and n cannot be equal or a multiple of each other, the least common multiple (LCM) is always larger than m and n.

Peptidic nanoparticles may be formed by the assembly of only one or more than one even unit (Table 2). Such peptidic nanoparticles represent topologically closed structures.

TABLE 2

Possible combinations of oligomerization states

| ID No. | m | n | Polyhedron Type | LCM | No. of Even Units | No. of Building Blocks |
|---|---|---|---|---|---|---|
| 1 | 5 | 2 | dodecahedron/icosahedron | 10 | 6 | 60 |
| 2 | 5 | 3 | dodecahedron/icosahedron | 15 | 4 | 60 |
| 3 | 4 | 3 | cube/octahedron | 12 | 2 | 24 |
| 4 | 3 | 4 | cube/octahedron | 12 | 2 | 24 |
| 5 | 3 | 5 | dodecahedron/icosahedron | 15 | 4 | 60 |
| 6 | 2 | 5 | dodecahedron/icosahedron | 10 | 6 | 60 |
| 7 | 5 | 4 | irregular | 20 | 1 | 20 |
| 8 | 4 | 5 | irregular | 20 | 1 | 20 |

Regular Polyhedra

Figure 3:
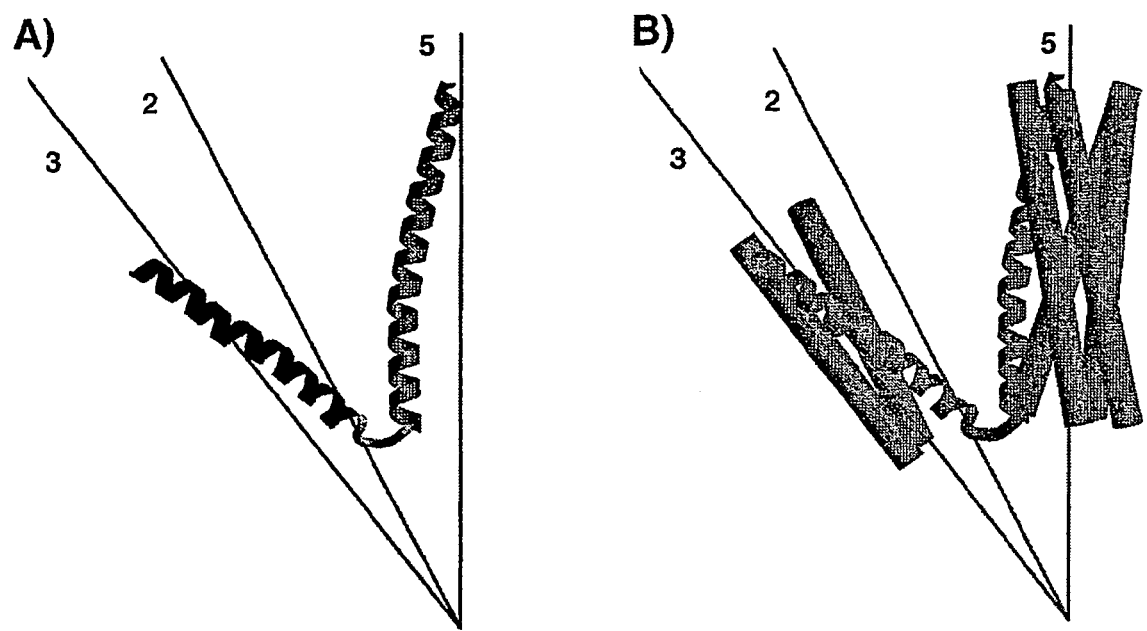
FIG. 3: Internal symmetry elements of the dodecahedron/icosahedron. The rotational symmetry axes (2-fold, 3-fold and 5-fold) are displayed as lines marked 2, 3 and 5. In A) a monomeric building block composed of oligomerization domain D1 (left, coiled-coil domain with three-fold symmetry), a linker segment L (bottom), and oligomerization domain D2 (right; coiled-coil domain with five-fold symmetry) is displayed such that the internal symmetry elements of the oligomerization domains D1 and D2 are superimposed onto the symmetry elements of the polyhedron. In B), the complete coiled-coil domains D1 and D2 are displayed. The additional symmetry objects generated by the 3-fold and the 5-fold rotational symmetry elements of the polyhedron are displayed as cylinders while the original molecule is displayed as a helix as in A).

There exist five regular polyhedra, the tetrahedron, the cube, the octahedron, the dodecahedron and the icosahedron. They have different internal rotational symmetry elements. The tetrahedron has a 2-fold and two 3-fold axes, the cube and the octahedron have a 2-fold, a 3-fold and a 4-fold rotational symmetry axis (FIG. 2A), and the dodecahedron and the icosahedron have a 2-fold, a 3-fold and a 5-fold rotational try axis (FIG. 2B). In the cube the spatial orientation of these axes is exactly the same as in the octahedron, and also in the dodecahedron and the icosahedron the spatial orientation of these axes relative to each other is exactly the same. Hence, for the purpose of peptidic nanoparticles of the invention the cube and the octahedron, and similarly the dodecahedron and the icosahedron can be considered to be identical. The cube/octahedron is built up from 24 identical three-dimensional building blocks, while the dodecahedron/icosahedron is built up from 60 identical three-dimensional building blocks (Table 2). These building blocks are the asymmetric units (AUs) of the polyhedron. They are tri-pyramids and each of the pyramid edges corresponds to one of the rotational symmetry axes, hence these AUs will carry at their edges 2-fold, 3-fold, and 4-fold or 5-fold symmetry elements depending on the polyhedron type. If these symmetry elements are generated from peptidic oligomerization domains such AUs are constructed from monomeric building blocks as described above. It is sufficient to align the two oligomerization domains D1 and D2 along two of the symmetry axes of the AU (FIG. 3). If these two oligomerization domains form stable oligomers, the symmetry interface along the third symmetry axis will be generated automatically, and it may be stabilized by optimizing interactions along this interface, e.g. hydrophobic, hydrophilic or ionic interactions, or covalent bonds like disulfide bridges (see e.g. Example 5).

Assembly to Peptidic Nanoparticles with Regular Polyhedral Symmetry

To generate peptidic nanoparticles with a regular geometry (dodecahedron, cube), more than one even unit is needed. E.g. to form a dodecahedron from a monomer containing trimeric and pentameric oligomerization domains, 4 even units, each composed of 15 monomeric building blocks are needed, i.e. the peptidic nanoparticle with regular geometry will be composed of 60 monomeric building blocks. The combinations of the oligomerization states of the two oligomerization domains needed and the number of even units to form any of the regular polyhedra are listed in Table 2.

Figure 4A:
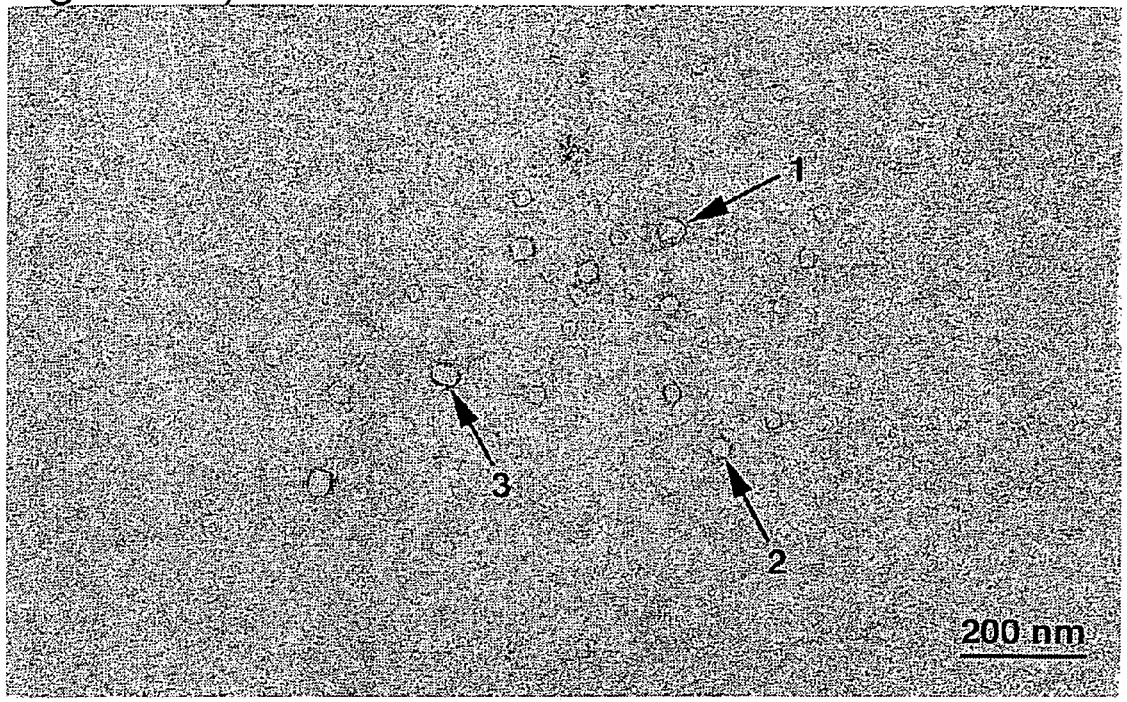
FIG. 4: Electron microscope picture of the peptidic nanoparticles formed from peptides with the sequence SEQ ID NO:1. A) The peptidic nanoparticles formed under reducing conditions (Example 1, Preparation 2); B) The peptidic nanoparticles formed under denaturing conditions (Example 1, Preparation 3). The pictures were prepared by negative staining with 2% uranyl acetate; the concentration of the peptide was 0.01 mg/ml. In A) the average diameter of the particles is roughly 25 nm. Particle No. 1 represents presumably a dodecahedron, particle No. 2 a cube, while particle No. 3 might represent a mixture of both, a so-called pentagonal prism. In B) the average diameter of the particles is roughly 15 nm.

Whether the even units will further assemble to form regular polyhedra composed of more than one even unit depends on the geometrical alignment of the two oligomerizations domains D1 and D2 with respect to each other, especially on the angle between the rotational symmetry axes of the two oligomerization domains. This is governed by i) the interactions at the interface between neighbouring domains in a nanoparticle, ii) the length of the linker segment L, iii) the shape of the individual oligomerization domains. This angle is larger in the even units compared to the arrangement in a regular polyhedron. Also this angle is not identical in monomeric building blocks as opposed to the regular polyhedron. If this angle is restricted to the smaller values of the regular polyhedron (by means of hydrophobic, hydrophilic or ionic interactions, or a covalent disulfide bridge) and the linker segment L is short enough, a given number of topologically closed even units each containing a defined number of monomeric building blocks will then further anneal to form a regular polyhedron (Table 2), or enclose more monomeric building blocks to from nanoparticles lacking strict internal symmetry of a polyhedron (FIG. 4A, see e.g. Example 1, Preparation 4).

The size of the peptidic nanoparticles then will mainly depend on two parameters: i) the shape (diameter and length) of the oligomerization domains D1 and D2 and ii) the length of the linker segment L. Coiled-coil oligomerization domains are slim, hence their diameter across the symmetry axis is small. Therefore, they can be arranged around the symmetry axes of the polyhedron rather closely to the polyhedron center. Oligomerization domains with a larger diameter can only be placed around the symmetry axes more distant from the polyhedron center to avoid overlap with each other. The size of the particle will be increased when using e.g. the foldon domain of T4 as an oligomerization domain.

While the size of the oligomerization domain is restrictive for the closest possible arrangement of the domains relative to the particle center, the length of the linker segment L will be limiting for the largest possible distance of the oligomerization domains to the polyhedron center. If the linker segment L is long, the oligomerization domains can still be arranged around the symmetry axis, while being more distant from each other. In such an arrangement, however, the particle will be only relatively loosely packed because the oligomerization domains do not pack closely to each other. A shorter linker will bring the oligomerization domains closer to each other and the interaction between the oligomerization domains will be more important and the packing of the particle will be more dense and confined. But unless the oligomerization domains have the shape of a cone, the interaction between the domains may still be rather small. In the case of the coiled-coil folding motif the interaction between the domains is restricted to about two helical turns (FIG. 3A). This is relatively little compared to the length of the interactions within the oligomerization domains themselves along their symmetry axis. In the case of the coiled-coil folding motif of 5 heptads this corresponds to 10 helical turns, hence the interaction between the two different oligomerization domains is significantly less dominant than the interaction between the helices of one single oligomerization domain. This means that the particle may form even when the non-bonded interactions between the two oligomerization domains within the nanoparticle are not very favorable. By optimizing these interactions the packing and stability of the particle may, however, be significantly improved. This can be achieved by optimizing the hydrophobic and the ionic interactions between the two oligomerization domains or by chemical cross-linking of the two domains with e.g. a disulfide bridge between the domains. When the two oligomerization domains are coiled-coils this may be achieved by a cystein residue at the outside of each of the helices, preferably in positions aa(f) of the heptad repeat. These cysteins can then form a disulfide bond and chemically cross-link the two oligomerization domains together.

The linker segment L may not be too short to avoid disruption of the protein fold of the oligomerization domains. If it is too short it will either disrupt proper folding of the individual oligomerization domains in the dense packing of the peptidic nanoparticle, or the peptidic nanoparticle may not form if the fold of the oligomerization domains is too stable to allow for the additionally needed flexibility of the linker.

It should be noted that such peptidic nanoparticles may be constructed from D-amino acids with the same oligomerization properties as L-amino acids. The peptidic nanoparticles will then simply be the enantiomeric form of the particles formed by L-amino acids. Such particles will have the advantage that they are much less biodegradable due to the decreased susceptibility to proteolysis, and hence their lifetime in the body will be substantially increased. This is especially advantageous for oral administration of the peptidic nanoparticles or for eliciting a strong immune response in the case when the peptidic nanoparticles are to be used as antigen display systems for vaccination.

On the other hand, to reduce immunogenicity of the peptidic nanoparticles, the sequence of the monomeric building blocks can be designed so as to include protease sensitive sites. This will reduce the circulation time of the peptidic nanoparticles. If the main portion of particles is quickly cleared from the blood stream due to an efficient binding to the target entity because of the cooperative binding effect of its targeting entities when displayed as multiple copies on the surface of the peptidic nanoparticles a reduced lifetime will be advantageous to avoid side-effects due to a strong immune response.

Functionalized Peptidic Nanoparticles

Targeting Entity

To prepare functionalized peptidic nanoparticles, the monomeric building blocks D1-L-D2 are modified to include at either end of the peptide sequence a targeting entity. On assembly to a peptidic nanoparticle, this targeting entity will then be displayed in multiple copies on the surface of the peptidic nanoparticles. Targeting entity is any molecule, which is specific for its corresponding receptor molecule, e.g. a ligand which is capable of binding a receptor.

Targeting entities are, for example, a peptide like somatostatin or an analogue thereof. Somatostatin is a cyclic tetradecapeptide hormone specific for the somatostatin receptors. Synthetic somatostatin analogues are e.g. octreotide, an octapeptide with one disulfide bridge, or SOM230. Other peptidic hormones useful as targeting entities include the gastrin releasing peptide/bombesin (GRP), the alpha melanocyte stimulating hormone ($\alpha$-MSH), vasoactive intestinal peptide (VIP), neurotensin, cholecystokinin, substance P, glucagonlike peptide and others. International Patent Application WO 98/10795 and WO 99/13329 describe tumor homing molecules, which can be used as target entities for tumors. Arap et al. (Science 1998, 279:377-80) describe selection of peptides, which target tumor blood vessels. Likewise, antibodies or antigen binding domains can be used as targeting entities.

Nonpeptidic biomolecules useful as targeting entities are, for example, sugar moieties, such as sugar moieties selectively binding to the asialoglycoprotein receptor and hence to the liver. Any cell-type specific receptor may be targeted by using its receptor specific biomolecule as a targeting entity. International Patent Application WO 93/18793 and U.S. Pat. Nos. 5,762,918 and 5,474,765 describe steroids linked to polyanionic polymers, which bind to vascular endothelial cells. Other targeting entities considered are the V3 loop of the gp120 of HIV (linkage with CD4, for the treatment of HIV), transferrin (binding to the transferrin receptor), or the LDLs (linkage to the LDL receptors).

Displaying these targeting entities in multiple copies on the surface of the peptidic nanoparticles increases their binding to the receptor molecule significantly due to the cooperative effect. If more than one receptor molecule is expressed on the surface of the target cell, cooperative binding of the peptidic nanoparticle will increase its specificity of binding to the target cell, similar to the binding of galactose or N-acetyl-galactosamine residues, when displayed on tri- or tetra-antennary N-linked glycans to the asialoglycoprotein receptor.

Furthermore, if the density of the receptor molecule is increased on a specific target cell as frequently encountered with cancer cells, the specificity of the functionalized peptidic nanoparticles for the cancer cell relative to other cells (with lower density of the same receptor molecules) will be increased due to the cooperativity of binding of the peptidic nanoparticles to the receptors. Therefore, among the potential biomolecules, the regulatory peptides are of special interest as targeting entities because of the high expression of their receptor on different malignancies.

The inventive peptidic nanoparticles also comprise targeting entities having the same or different specificities in order to bind to the same or to distinct acceptors. It will be very easy to prepare such hybrid peptidic nanoparticles by coassembling monomeric building blocks with the same core domains (the two linked oligomerization domains D1 and D2) but carrying different targeting entities. One targeting entity may be e.g. octreotide to target the peptidic nanoparticles to the cancer cell, the other targeting entity the RGD sequence as a binding partner for the integrins.

Drug Delivery

Peptidic nanoparticles can further be functionalized to act as a carrier vesicle for a drug. A drug molecule is attached at either end or within the peptide sequence of the monomeric building block, preferably at the end, which is not yet modified by a targeting entity. The inventive peptidic nanoparticles may also comprise units having different drugs attached to it in order to act as a multiple drug delivery system.

In general, two classes of drugs are contemplated for use in the present invention: bioaffecting molecules and diagnostic molecules.

Bioaffecting molecules are any, which affect cell and body functions, either positively or negatively. This class includes toxins, cytotoxics, cytostatics, hormones, neurotransmitters, biologically active peptides, radionuclides, antibiotics, antipyretics, analgesics and antiinflammatory drugs, expectorants, sedatives, muscle relaxants, antiepileptics, antiulcer drugs, antidepressants, antiallergic drugs, cardiotonic drugs, antiarrythmic agents, vasodilators, antihypertensives, anticoagulants, haemostatic agents and the like.

Suitable toxins, according to the invention, include, but are not limited to, ricin, abrin, diphtheria toxin, modecin, tetanus toxin, mycotoxins, mellitin, α-amanitin, pokeweed antiviral protein, ribosome inhibiting proteins, especially those of wheat, barley, corn, rye, gelonin and maytansinoid. Suitable cytotoxic agents, according to the invention, include, but are not limited to alkylating agents such as chlorambucil, cyclophosphamide, melphalan, cyclopropane; anthracycline antitumor antibiotics such as doxorubicin, daunomycin, adriamycin, mitomycin C, 2-(hydroxymethyl)anthraquinone; antimetabolites such as methotrexate, dichloromethatrexate, cisplatin, carboplatin, and metallopeptides containing platinum, copper, vanadium, iron, cobalt, gold, cadmium, zinc and nickel. Other agents include DON, thymidine, pentamethylmelamin, dianhydrogalactitol, 5-methyl-THF, anguidine, maytansine, neocarzinostatin, chlorozotocin, AZQ, 2'-deoxycoformycin, PALA, AD-32, m-AMSA and misonidazole.

A compendium of drugs that may be used is found in Gilman et al., Goodman and Gilman's The Pharmacologic Basis of Therapeutics, MacMillan, New York, 10$^{th}$ edition 2001.

Diagnostic molecules are those, which can be detected in the body without recourse to invasive procedures such as surgery. Such molecules include fluorescent compounds, radiolabeled compounds, X-ray opaque dyes, ferromagnetic compounds, and the like.

The N- or C-terminus of the monomeric building block can be modified easily, e.g. by introducing peptide ligands like a cytotoxic tail, or a His-tail to chelate different toxic drugs (e.g. heavy metals). Thus release of the heavy metal within the blood stream should be minimal, whilst release would take place in acidic environments, for instance in certain parts of a cell in the lysosomes, where the pH is around 5.5.

In a preferred embodiment of this invention, the bioaffecting molecule is a radionuclide, which is attached to the peptidic nanoparticle by means of a chelator. Suitable chelators for the binding of radionuclides, according to the invention, include, but are not limited to, diethylenetriamine pentaacetic acid (DTPA), isothiocyanato-diethylenetriamine pentaacetic acid (ITC-DTPA), ethylenedinitrile tetraacetic acid (EDTA), tetraazocyclododecane-1,4,7,10-tetraacetic acid (DOTA), cyclohexane-1,2-diamino-N,N'-diacetate (CHTA), and 2-(4-isothiocyanatobenzyl)-6-methyl-diethylenetriamine pentaacetic acid (MX-DTPA). Radioisotopes useful as therapeutic entities are described in Kairemo et al. (Acta Oncol. 1996, 35:343-55), and include Y-90, I-123, I-125, I-131, Bi-213, At-211, Cu-67, Sc-47, Ga-67, Rh-105, Pr-142, Nd-147, Pm-151, Sm-153, Ho-166 Gd-159, Tb-161, Eu-152, Er-171, Re-186, and Re-188.

Linking Targeting Entity and Drugs to the Oligomerization Domain

The targeting entity as well as the bioaffecting molecule, e.g. drug, diagnostic molecule or chelator, may be attached to the peptidic nanoparticle by chemical crosslinking. In a preferred embodiment of this invention, the individual units may be connected via a peptide bond and/or a peptidic linker. Other chemical crosslinks include disulfide bonds, e.g. spontaneously, or via one or more linker molecules. Such linker molecules are molecules bearing two or more reactive groups like —SH, —N$_3$, —COOH, —COBr, —COCl, —NH$_2$ or —CHO.

It should be noted that the typical arrangement used in such systems is to link the targeting entity and/or the bioaffecting molecule to the peptidic nanoparticle via a single bond or via a relatively short chemical linker. Examples of such linkers include succinimidyl 4-(N-maleimidomethyl)cyclohexane-1-carboxylate (SMCC) or the linkers disclosed in U.S. Pat. No. 4,880,935, and oligopeptide spacers.

Examples are N-5-azido-2-nitrobenzoyloxysuccinimide, p-azidophenacylbromide, p-azido-phenyl glyoxal, N-4-(azidophenylthio)phthalimide, bis(sulfosuccinimidyl)suberate, bis-maleimidohexane, bis[2-(succinimidooxycarbonyloxy)ethyl]sulfone, 1,5-difluoro-2,4-dinitro-benzene, 4,4'-diisothiocyano-2,2'-disulfonic acid stilbene, dimethyl adipimidate, dimethyl pimelimidate, dimethyl suberimidate, dithiobis(succinimidylpropionate), disuccinimidyl suberate, disuccinimidyl tartrate, dimethyl 3,3'-dithiobispropionimidate, 4,4'-dithiobis-phenylazide, 3,3'-dithiobis(succinimidylpropionate), ethyl-4-azidophenyl-1,4-dithio-butyrimidate, 1-azido-4-fluoro-3-nitrobenzene, N-hydroxysuccinimidyl-4-azidobenzoate, methyl-4-azidobenzoimidate, m-maleimidobenzoyl-N-hydroxysulfo-succinimide ester, N-hydroxysuccinimidyl-4-azidosalicylic acid, p-nitrophenyl-2-diazo-3,3,3-trifluoropropionate, N-succinimidyl (4-azidophenyl)-1,3'-dithiopropionate, sulfosuccinimidyl 2-(m-azido-o-nitrobenzamido)-ethyl-1,3'-dithiopropionate, N-succinimidyl-6-(4'-azido-2'-nitrophenyl-amino)hexanoate, sulfosuccinimidyl 2-(p-azidosalicylamido)ethyl-1, 3'-dithiopropionate, N-succinimidyl(4-iodoacetyl)aminobenzoate, succinimidyl 4-(N-maleimidomethyl)-cyclohexane-1-carboxylate, succinimidyl 4-(p-maleimidophenyl)butyrate, N-succinimidyl 3-(2-pyridyidithio)propionate, bis[2-(sulfosuccinimidooxycarbonyloxy)ethyl]sulfone, disulfosuccinimidyl tartrate, ethylene glycolbis(sulfosuccinimidylsuccinate), m-maleimido-benzoyl-N-hydroxysulfosuccinate, sulfosuccinimidyl (4-azidophenyldithio)propionate, sulfosuccinimidyl 6-(4'-azido-2'-nitrophenylamino)hexanoate, sulfosuccinimidyl (4-iodo-acetyl)aminobenzoate, sulfosuccinimidyl 4-(N-maleimidomethyl)cyclohexane-1-carboxylate, sulfosuccinimidyl 4-(p-maleimidophenyl)butyrate, and 2-iminothiolane.

If the link between the bioaffecting molecule and the peptidic nanoparticle is covalent, the linkage must be cleavable in vivo if the drug has to be released from the peptidic nanoparticle to be fully bioactive. The linkage can be selected so as to allow the drug to be cleaved from the carrier in the desired target area. The cleavage may be hydrolytic cleavage, which takes place at acidic pH but not at neutral or slightly alkaline pH. Thus cleavage of the conjugate within the blood stream should be minimal, whilst cleavage would take place when the conjugate is in acidic environments, for instance in certain parts of a cell in the lysosomes, where the pH is around 5.5.

Preferably, however, the linkage is selected so as to be capable of enzymatic cleavage, preferably by enzymes present only in selected cells or selected parts of cells. Particularly suitable peptide linkers are those which act as a specific substrate for thiol proteinases or other proteases, known to be present in lysosomes like cathepsins B and L. Such peptides sequences may be Ala-Leu-Ala-Leu, Gly-Phe-Leu-Gly, Gly-Phe-Ala-Leu or various di-, tri-, and tetrapeptides containing Ala and Leu, or peptide sequences containing a basic amino acid at the P1 site and a hydrophobic amino acid at the P2 site.

As an alternative the drug may be attached to the peptidic nanoparticle by other means than covalent linkage if the monomeric building block contains a polylysine (sequence which allows the attachment of the drug, especially when it is a nucleic acid), a polyarginine, or a transferrin/poly-L-lysine complex, which combines with the said nucleic acid sequence or with the said protein to form a conjugate.

In a preferred embodiment of the invention, two or more identical monomeric building blocks of formula (I), each carrying a different substituent, e.g. one carrying a targeting entity and another one carrying a drug, are co-assembled to multifunctional nanoparticles. This is an especially easy way to non-covalently link a drug to a targeting entity.

Therapeutic and Diagnostic Method

The invention relates to a therapeutic method for treating a human having a diseased organ or tissue, comprising administering an effective amount of the peptidic nanoparticle based drug targeting system of the present invention to the human to affect the metabolism of cells expressing receptors for the targeting entity on their surfaces or nearby cells, said cells being among those of the diseased organ or tissue. In particular, the invention relates to a method for the treatment of a disease which responds to a drug, which comprises administering a functionalized peptidic nanoparticles substituted with said drug.

The invention further relates to a diagnostic method for determining whether a human has a diseased organ or tissue, comprising administering an effective amount of the peptidic nanoparticle based drug targeting system, i.e. a drug which is a diagnostic molecule, to the human and noninvasively detecting the localization of said drug.

Vaccination

To prepare functionalized peptidic nanoparticles, the monomeric building blocks D1-L-D2 are modified to include at either end or at both ends of the continuous chain an antigen, preferably a peptidic antigen. On assembly to a peptidic nanoparticle, the antigen will then be displayed in multiple copies on the surface of the peptidic nanoparticles thus representing an ordered and repetitive antigen or antigenic determinant array, which can be used as an antigen display system. Such a rigid, repetitive antigen display predictably elicits high titer of serospecific neutralizing antibodies, since B cells react against highly repetitive, rigidly ordered antigenic determinants with short-lived IgM responses even without the need of T help (Tl-1 immune response). In addition, the particulate structure will guide it to antigen presenting cells and induce CD4 proliferative responses and cytotoxic T lymphocytes, thus inducing long-term immunologic memory.

Peptidic antigens of the invention may be selected from the group consisting of (a) proteins suited to induce an immune response against cancer cells; (b) proteins suited to induce an immune response against infectious diseases; and (c) proteins suited to induce an immune response against allergens. Peptidic nanoparticles comprising such proteins or peptidic fragments thereof may be suited to induce an immune response in humans, or also in farm animals. Combinations of one or more B-cell and T-cell epitopes within one nanoparticle may also be generated to elicit a multispecific immune response.

In one specific embodiment of the invention, the antigen or antigenic determinant is one that is useful for the prevention of infectious disease. Such treatment will be useful to prevent a wide variety of infectious diseases affecting a wide range of hosts, e.g. humans or non-human animals, such as cow, sheep, pig, dog, cat, other mammalian species and non-mammalian species as well. Treatable infectious diseases are well known to those skilled in the art. Examples include infections of viral etiology such as HIV, influenza, herpes, viral hepatitis, Epstein Bar, polio, viral encephalitis, measles, chicken pox, and the like, or infections of bacterial etiology such as pneumonia, tuberculosis, syphilis, and the like, or infections of parasitic etiology such as malaria, trypanosomiasis, leishmaniasis, trichomoniasis, amoebiasis, and the like. Particular examples of antigens or antigenic determinants include the HIV antigens gp 41 and gp 120, the influenza antigens hemagglutinin and neuraminidase, hepatitis B surface antigen, and circumsporozoite protein of malaria.

In another specific embodiment, the compositions of the invention are immunotherapeutics that may be used for the treatment of allergies or cancer. The selection of antigens or antigenic determinants for the composition and the method of treatment for allergies would be known to those skilled in the medical art treating such disorders. Representative examples of this type of antigen or antigenic determinant include bee venom phospholipase A2, Bet v 1 (birch pollen allergen), 5 Dol m V (white-faced hornet venom allergen), and Der p 1 (House dust mite allergen).

In a preferred aspect of the invention, a composition for the prevention and treatment of malaria is envisaged. The life cycle of the malaria parasite provides several stages at which interference could lead to cessation of the infective process. In the life cycle of the malaria parasite, a human becomes infected with malaria from the bite of a female Anopheles mosquito. The mosquito inserts its probe into a host and in so doing, injects a sporozoite form of Plasmodium falciparum, present in the saliva of the mosquito. Over the years, it has become increasingly clear that a malaria vaccine should incorporate different antigenic regions of a variety of parasite cell surface proteins, resulting in a multi-component and multi-stage vaccine. Possible protein and peptide sequences suitable for the design of a peptide vaccine may contain sequences from the following Plasmodium falciparum proteins: MSP-1 (a large polymorphic protein expressed on the parasite cell surface), MSA1 (major merozoite surface antigen 1), CS protein (native circumsporozoite), 35 KD protein or 55 KD protein or 195 KD protein according to U.S. Pat. No. 4,735,799, or AMA-1 (apical membrane antigen 1).

In another preferred aspect of the invention, a composition for the prevention and treatment of HIV is envisaged. For the preparation of an anti HIV vaccine a synthetic peptide capable of eliciting HIV-specific antibodies may be used, said synthetic peptide having the amino acid sequence of a functional T-cell epitope or B-cell epitope of an envelope or gag protein or gp120 or gp41 of HIV-1 to provide an immune response. Of special interest are sequences within gp41, which can induce conformation specific neutralizing antibodies able to interfere with the fusion process like the known antibody 2F5. Such sequences are mainly localized in and around the HR1 and HR2 and the cluster I and cluster II regions. Antibodies binding to e.g. the coiled-coil trimer of gp41 and elicited by peptidic nanoparticles of the invention incorporating this coiled-coil trimer will inhibit hairpin formation and hence viral fusion. Similarly, antibodies raised against the trimeric coiled-coil of Ebola or of another virus with a similar fusion process will inhibit viral entry of these viruses.

The selection of antigens or antigenic determinants for the composition and method of treatment for cancer would be known to those skilled in the medical art treating such disorders. Representative examples of this type of antigen or antigenic determinant include the following: HER2/neu (breast cancer), GD2 (neuroblastoma), EGF-R (malignant glioblastoma), CEA (medullary thyroid cancer), CD52 (leukemia), MUC1 (expressed in hematological malignancies), gp100 protein, or the product of the tumor suppressor gene WT1.

The use of nanoparticles of the invention as adjuvants is also envisaged.

The invention also concerns a method of vaccination, which comprises administering an effective amount of a functionalized peptidic nanoparticles substituted with an antigen as described hereinbefore.

Pharmaceutical Compositions

The present invention relates also to pharmaceutical compositions comprising peptidic nanoparticles of the invention, in particular nanoparticles carrying a targeting entity and a drug, or nanoparticles carrying an antigen. Compositions for enteral administration, such as nasal, buccal, rectal or oral administration, also including nebulizers and eye drops, and for parenteral administration, such as intravenous, intramuscular or subcutaneous administration, to warm-blooded animals, especially humans, are preferred. Particularly preferred are compositions for parenteral administration. Further compositions considered are those suitable for surgery implant. The compositions comprise the peptidic nanoparticles alone or, preferably, together with a pharmaceutically acceptable carrier. The dosage of the active ingredient depends upon the disease to be treated and upon the species, its age, weight, and individual condition, the individual pharmacokinetic data, and the mode of administration.

The pharmaceutical compositions comprise from approximately 1% to approximately 95% of the active ingredient. Unit dose forms for parenteral administration are, for example, ampoules or vials, e.g. vials containing from about 0.01 mg to about 1.0 g peptidic nanoparticles. Further dosage forms considered are, for example, ointments, creams, pastes, foams, tinctures, dispersions, and the like.

Preference is given to the use of solutions of the peptidic nanoparticles, and also suspensions or dispersions, especially isotonic aqueous solutions, dispersions or suspensions which, for example in the case of lyophilised compositions comprising the active ingredient alone or together with a carrier, for example mannitol, can be made up before use. The pharmaceutical compositions may be sterilized and/or may comprise excipients, for example preservatives, stabilizers, wetting agents and/or emulsifiers, solubilizers, salts for regulating osmotic pressure and/or buffers and are prepared in a manner known per se, for example by means of conventional dissolving and lyophilising processes. The said solutions or suspensions may comprise viscosity-regulating agents.

For parenteral administration, aqueous solutions of the peptidic nanoparticles or aqueous injection suspensions that contain viscosity-regulating substances and, if desired, stabilizers, are especially suitable. The peptidic nanoparticle, optionally together with excipients, can also be in the form of a lyophilisate and can be made into a solution before parenteral administration by the addition of suitable solvents.

The invention relates also to processes and to the use of peptidic nanoparticles for the manufacture of pharmaceutical preparations, which comprise peptidic nanoparticles of the invention, in particular nanoparticles carrying a targeting entity and a drug, or nanoparticles carrying an antigen, as active ingredient. The pharmaceutical compositions of the present invention are prepared in a manner known per se, for example by means of conventional mixing, granulating, coating, dissolving or lyophilising processes.

Monomeric Building Blocks and Manufacture of Peptidic Nanoparticles and Functionalized Peptidic Nanoparticles The invention also concerns the monomeric building blocks of formula (I) as described hereinbefore, and such monomeric building blocks optionally carrying a targeting entity and a drug, or an antigen.

Monomeric building blocks according to the invention may be obtained by chemical synthesis or by expression in genetically modified organisms. Due to the relatively short length of the monomeric polypeptide chains, chemical synthesis is preferred. Methods of synthesis of polypeptides are well known, and may easily be adapted to produce monomeric building blocks of the invention. Preferred is standard peptide chemistry starting the peptide synthesis from the C-terminus. Ligands at the N-terminal may be attached under standard peptide synthesis conditions. Alternatively, the monomeric building blocks can be expressed directly in a genetically engineered multicellular organism using established transcription-translation systems.

Peptidic nanoparticles are obtained by equilibrating monomeric building blocks in aqueous solution, preferably in aqueous buffer solution around neutrality, e.g. in sodium chloride solution containing Tris buffer. Peptides containing cysteine residues may be handled by addition of dithiothreitol (DTT), which may be added at some stages of equilibration to reduce disulfide bridges and to allow reformation of new disulfide bridges. For proper folding of the peptidic nanoparticles, especially those containing disulfide bridges, refolding of the nanoparticle may be started from denaturing conditions (8 M urea) and then dialyzing it to native conditions (e.g. 150 mM NaCl, pH 7.5) either under reducing or oxidizing conditions.

EXAMPLES

The following examples are useful to further explain the invention but in no way limit the scope of the invention.

Example 1

Ac-COMP—Trimer(De Novo)-$NH_2$

A peptide of the following sequence (SEQ ID NO:1) is prepared by standard solid phase peptide synthesis (Merrifield R. B., Adv Enzymol Relat Areas Mol Biol. 1969, 32:221-296) starting the synthesis from the C-terminus.

```
   1         10         20         30         40
Ac-DEMLRELQETNAALQDVRELLRQQVKQITFLKCLLMGGRLLCRLEEL 50        60
ERRLEELERRLEELERR-NH2
```

This corresponds to 30 amino acids from the pentameric domain of COMP (Cartilage Oligomerization Matrix Protein) lacking the disulfide bridges at the C-terminal end and with improved N- and C-termini for stable intra- and interhelical interactions, two glycine residues as the linker segment; and 26 amino acids as a de novo designed trimeric coiled-coil domain. At the N-terminus the positively charged amino group is replaced by an acetylamino moiety, at the C-terminus the negatively charged carboxy group is replaced by a carboxamide. Residues 33 and 42 are cysteine residues; they are at aa(f) positions of the respective coiled coils, possibly forming an interhelical disulfide bridge between the two helices.

Four different conditions are tested for assembling nanoparticles from the monomeric building block SEQ ID NO:1 for determining optimal refolding conditions of this peptide which is able to form an intramolecular disulfide bridge.

Solubilization:

Preparation 1 (oxidizing conditions): 1 mg/ml peptide is dissolved directly in 150 mM NaCl, 20 mM Tris, pH 7.5.

Preparation 2 (reducing conditions): 1 mg/ml peptide is dissolved directly in 150 mM NaCl, 20 mM Tris, pH 7.5; 2 mM DTT.

Preparation 3 (denaturing conditions): 0.07 mg/ml peptide is dissolved in 150 mM NaCl, 20 mM Tris, pH 7.5; 2 mM DTT, 8 M urea. The solution is dialyzed in steps from 150 mM NaCl, 20 mM Tris, pH 7.5; 8 M urea/4 M urea/2 M urea/no urea. The solution is concentrated to 1 mg/ml in 150 mM NaCl, 20 mM Tris, pH 7.5.

Preparation 4 (denaturing, reducing conditions): 0.07 mg/ml peptide is dissolved in 150 mM NaCl, 20 mM Tris, pH 7.5; 8 M urea, 2 mM DTT. The solution is dialyzed in steps from 150 mM NaCl, 20 mM Tris, pH 7.5; 8 M urea and 2 mM DTT/4 M urea and 2 mM DTT/2 M urea and 2 mM DTT/no urea and 2 mM DTT/no urea and no DTT. The solution is concentrated to 1 mg/ml in 150 mM NaCl, 20 mM Tris, pH 7.5.

Analytical Ultracentrifugation (AUC):

From preparation 1: The AUC reveals three major components of roughly identical fraction size with a molecular weight (MW) of 383, 997 and 2210 kDa, respectively, corresponding to peptidic nanoparticles containing 48.5, 126.4 and 280.1 monomers.

From preparation 2: The main fraction (80%) of this AUC measurement is a component with a MW of 168 and two minor fractions with a MW of 330 and 131 kDa, respectively, corresponding to peptidic nanoparticles containing 21.3, 41.8 and 16.6 monomers. The latter corresponds to peptidic nanoparticles as even units composed of 15 monomeric building blocks with a theoretical MW of 118.3 kDa.

From preparation 3: The measured MW is slightly concentration dependent. At lower concentrations (0.15 mg/ml and 0.3 mg/ml) the peptidic nanoparticle is composed of 3 even units, at higher concentrations (0.4 mg/ml, 0.6 mg/ml and 0.8 mg/ml) the peptidic nanoparticle is composed of 4 even units. This peptidic nanoparticle with 4 even units has the molecular weight of a regular polyhedron with dodecahedral symmetry, which is composed of 60 monomeric building blocks.

| Concentration | MW kDa | No. of monomers | No. of even units |
|---|---|---|---|
| 0.15 mg/ml | 347 | 43.9 | 2.9 |
| 0.3 mg/ml | 356 | 45.1 | 3.0 |
| 0.4 mg/ml | 461 | 58.4 | 3.9 |
| 0.6 mg/ml | 437 | 55.3 | 3.7 |
| 0.8 mg/ml | 489 | 61.9 | 4.1 |

From preparation 4: The measured MW is concentration dependent and at higher concentrations the peptidic nanoparticles contain as many as 121 monomeric building blocks.

| Concentration | MW kDa | No. of monomers | No. of even units |
|---|---|---|---|
| 0.15 mg/ml | 633 | 80.1 | 5.3 |
| 0.25 mg/ml | 718 | 90.9 | 6.1 |
| 0.8 mg/ml | 960 | 121.5 | 8.1 |

Electron Microscopy (EM):

From preparation 1: As judged from the EM pictures the peptides do not form peptidic nanoparticles but rather form irregular aggregates.

From preparation 2: The peptides form peptidic nanoparticles of different size and also the shape is not always completely spherical. The average size of the peptidic nanoparticles is 25 nm (FIG. 4A).

Figure 4B:
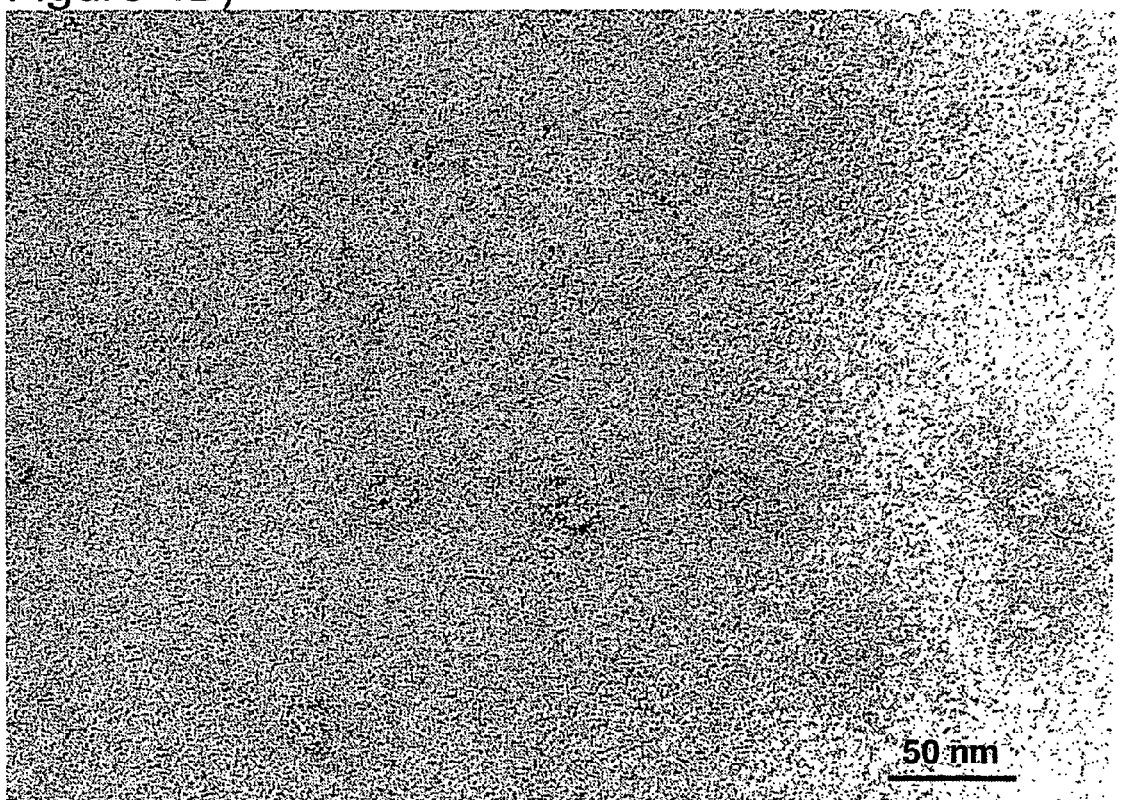

From preparation 3: The peptides form peptidic nanoparticles of identical size with spherical appearance. The diameter of the peptidic nanoparticles is 15 nm and corresponds to the predicted value from molecular modeling for a regular polyhedron with dodecahedral symmetry (FIG. 4B).

From preparation 4: The peptides form peptidic nanoparticles of nearly identical size with mostly spherical appearance. The diameter of the peptidic nanoparticles is 15 nm and corresponds to the predicted value from molecular modeling for a regular polyhedron with dodecahedral symmetry.

Example 2

COMP—Trimer(De Novo) (No Cys)

A peptide of the following sequence (SEQ ID NO:2) is recombinantly expressed in a standard *E. coli* expression system using a His-tag affinity purification scheme in combination with a thrombin cleavage:

```
         10        20        30        40
GSDEMLRELQETNAALQDVRELLRQQVKQIRRLKRLLRGGRLLAELEEL 50        60
RERLEELERRLEELERR
```

This is related to the sequence from Example 1 (SEQ ID NO:1) but with improved intra-molecular ionic interactions between the two helices of the nanoparticle (residues 31, 32, 35, 38, 45, 50, 51), lacking the intra-molecular disulfide bridge between residues 33 and 42 of Example 1 (replacement of cysteine by arginine or alanine, respectively) and starting with two additional residues (glycine and serine) from the thrombin cleavage site of the expression system.

One condition was tested for assembling nanoparticles from the monomeric building block SEQ ID NO:2: 1 mg/ml peptide is dissolved in 150 mM NaCl, 20 mM Tris, pH 7.0. The measured MW corresponds to nanoparticles composed of about 148 monomers, a nanoparticle with more monomers than needed for a regular polyhedron with 60 asymmetric units. The two helices of the two oligomerization domains are not fixed by a disulfide bridge in their relative orientation to each other.

| Concentration | MW kDa | No. of monomers |
|---|---|---|
| 0.3 mg/ml | 1192 | 148 |

Example 3

Trimer(Foldon)—COMP

A peptide of the following sequence (SEQ ID NO:3) is recombinantly expressed in a standard *E. coli* expression system using a His-tag affinity purification scheme in combination with a thrombin cleavage:

```
          10        20        30        40
GSGYIPEAPRDGQAYVRKDGEWVLLSTFLGGLAPQMLRELQETNAALQD 50        60        70
VRELLRQQVKQITFLKNTVMECDACG
```

This corresponds to two additional residues (glycine and serine) from the thrombin cleavage site of the expression system, 27 amino acids of the trimeric foldon domain of fibritin; two glycine residues as the linker segment; and 44 amino acids from the pentameric domain of COMP including the disulfide bridges at the C-terminal end. Residues 71 and 74 may form interhelical disulfide bridges.

Two different conditions are tested for assembling nanoparticles from the monomeric building block SEQ ID NO:3.

Preparation 1: 1 mg/ml peptide is dissolved in 150 mM NaCl, 20 mM Tris, pH 7.0.

Preparation 2: 1 mg/ml peptide is dissolved in 150 mM NaCl, 20 mM Tris, pH 7.0; 2 mM DTT.

Analytical Ultracentrifugation:

From preparation 1: The measured MW is concentration dependent with increasing nanoparticle size upon increasing concentration.

| Concentration | MW kDa | No. of monomers |
|---|---|---|
| 0.3 mg/ml | 78 | 9.3 |
| 0.4 mg/ml | 82 | 9.9 |
| 0.6 mg/ml | 91 | 10.9 |
| 1.2 mg/ml | 93 | 11.2 |

From preparation 2: The measured MW is concentration independent and corresponds to nanoparticles composed of about 13 monomers.

| Concentration | MW kDa | No. of monomers |
|---|---|---|
| 0.3 mg/ml | 113 | 13.6 |
| 0.4 mg/ml | 102 | 12.3 |
| 0.6 mg/ml | 102 | 12.3 |
| 1.2 mg/ml | 103 | 12.4 |

Native Gel:

From preparation 1: The native gel reveals two major components corresponding to a molecular weight of the peptidic nanoparticles of about 66 kDa and 120 kDa, the latter one corresponding to a peptidic nanoparticle composed of 15 monomeric building blocks, i.e. one even unit.

Example 4

Trimer(Foldon)Cys11—COMP

A peptide of the following sequence (SEQ ID NO:4) is recombinantly expressed in a standard *E. coli* expression system using a His-tag affinity purification scheme in combination with a thrombin cleavage:

```
          10        20        30        40
GSGYIPEAPRCGQAYVRKDGEWVLLSTFLGGLAPQMLRELQETNAALQD 50        60        70
VRELLRQQVKQITFLKNTVMECDACG
```

This corresponds to two additional residues (glycine and serine) from the thrombin cleavage site of the expression system; 27 amino acids of the trimeric foldon domain of fibritin; two glycine residues as the linker segment; and 44 amino acids from the pentameric domain of COMP including the disulfide bridges at the C-terminal end. Residues 71 and 74 may form interhelical disulfide bridges. The residue Asp 11 is replaced by a cystein residue which will be able to form a disulfide bridge with the same residue of another monomeric building block to which it is symmetry related by the two-fold rotation axis of the dodecahedron.

Two Different Conditions are Tested for Assembling Nanoparticles from the Monomeric Building Block SEQ ID NO:4.

Preparation 1: 1 mg/ml peptide is dissolved in 150 mM NaCl, 20 mM Tris, pH 7.0.

Preparation 2: 1 mg/ml peptide is dissolved in 150 mM NaCl, 20 mM Tris, pH 7.0; 2 mM DTT.

Analytical Ultracentrifugation:

From preparation 1: The measured MW corresponds to nanoparticles composed of 9.0 monomers.

| Concentration | MW kDa | No. of monomers |
|---|---|---|
| 0.2 mg/ml | 75 | 9.0 |

From preparation 2: The measured MW corresponds to nanoparticles composed of 11.2 monomers.

| Concentration | MW kDa | No. of monomers |
|---|---|---|
| 0.2 mg/ml | 93 | 11.2 |

Example 5

Trimer(Foldon)Cys11—Linker—COMP

A peptide of the following sequence (SEQ ID NO:5) is recombinantly expressed in a standard *E. coli* expression system using a His-tag affinity purification scheme in combination with a thrombin cleavage:

```
          10        20        30        40
GSGYIPEAPRCGQAYVRKDGEWVLLSTFLGGSGLAPQMLRELQETNAAL 50        60        70
QDVRELLRQQVKQITFLKNTVMECDACG
```

This corresponds to the sequence from Example 4 (SEQ ID NO:4) with two additional residues (serine and glycine) between the foldon and COMP to increase flexibility of the two domains relative to each other.

Two different conditions were tested for assembling nanoparticles from the monomeric building block SEQ ID NO:5.

Preparation 1: 1 mg/ml peptide is dissolved directly in 150 mM NaCl, 20 mM Tris, pH 7.5, 2 mM DTT.

Preparation 2: 0.07 mg/ml peptide is dissolved in 150 mM NaCl, 20 mM Tris, pH 7.5, 8 M urea. The solution is dialyzed in steps from 150 mM NaCl, 20 mM Tris, pH 7.5, 8 M urea/4 M urea/2 M urea/no urea. The solution is concentrated to 1 mg/ml in 150 mM NaCl, 20 mM Tris, pH 7.5.

Analytical Ultracentrifugation:

From preparation 1: The measured MW is slightly concentration dependent and the solution contains a mixture of nanoparticles with different sizes.

| Concentration | MW kDa | No. of monomers |
|---|---|---|
| 0.3 mg/ml | 86 | 10.1 |
| 0.6 mg/ml | 83 | 9.8 |
| 1.2 mg/ml | 96 | 11.3 |

From preparation 2: The measured MW is concentration independent and the particles are composed of 15 monomers corresponding to one even unit.

| Concentration | MW kDa | No. of monomers |
|---|---|---|
| 0.24 mg/ml | 128 | 15.1 |
| 0.4 mg/ml | 122 | 14.3 |
| 1.2 mg/ml | 126 | 14.8 |

Example 6

Trimer(Foldon)Cys11—Linker 2—COMP

A peptide of the following sequence (SEQ ID NO:6) is recombinantly expressed in a standard *E. coli* expression system using a His-tag affinity purification scheme in combination with a thrombin cleavage:

```
         10        20        30        40
GSGYIPEAPRCGQAYVRKDGEWVLLSTFLGGSGSGLAPQMLRELQETNA 50        60        70
ALQDVRELLRQQVKQITFLKNTVMECDACG
```

This corresponds to the sequence from Example 4 (SEQ ID NO:4) with four additional residues (serine, glycine, serine and glycine) between the foldon and COMP to further increase the flexibility of the two domains relative to each other. One condition was tested for assembling nanoparticles from the monomeric building block SEQ ID NO:6: 1 mg/ml peptide is dissolved in 150 mM NaCl, 20 mM Tris, pH 7.0.

Analytical Ultracentrifugation

The measured MW is concentration independent and the molecular weight corresponds to nanoparticles composed of slightly less monomers than for one even unit.

| Concentration | MW kDa | No. of monomers |
|---|---|---|
| 0.4 mg/ml | 108 | 12.5 |
| 0.8 mg/ml | 116 | 13.5 |
| 1.2 mg/ml | 111 | 12.9 |

The invention claimed is:

1. A peptidic nanoparticle consisting of an assembly of 10 or more peptides, in which each peptide is consisting of a continuous chain of a peptidic oligomerization domain D1, a linker segment L, and a peptidic oligomerization domain D2 of formula (I):

D1-L-D2     (I), wherein
each D1 is a synthetic or natural peptide, and a plurality of D1 form at least one protein oligomer assembly $(D1)_m$, wherein the protein oligomer assembly consists of m subunits of D1,
each D2 is a synthetic or natural peptide, and a plurality of D2 form at least one protein oligomer assembly $(D2)_n$, wherein the protein oligomer assembly consists of n subunits of D2,
the peptidic nanoparticle contains:
(a) one of m or n is 2 forming a dimer protein oligomer assembly, and the other of m or n is 5 forming a pentamer protein oligomer assembly; or
(b) one of m or n is 3 forming a trimer protein oligomer assembly, and the other of m or n is 4 or 5 forming a tetramer or pentamer protein oligomer assembly, respectively; or
(c) one of m or n is 4 forming a tetramer protein oligomer assembly, and the other of m or n is 5 forming a pentamer protein oligomer assembly;
L is a short flexible linker segment,
at least one D1 or D2 is a coiled-coil peptide sequence, and
D1, D2 or L is optionally further substituted by a substituent selected from a targeting entity, drug and antigen.

2. A peptidic nanoparticle according to claim 1 wherein m or n is 5.

3. A peptidic nanoparticle according to claim 1 wherein at least one peptide is different from a viral capsid protein.

4. A peptidic nanoparticle according to claim 1 wherein at least one D1 and D2 are coiled-coil peptide sequences.

5. A peptidic nanoparticle according to claim 1 wherein at least one peptide is linked to a targeting entity.

6. A peptidic nanoparticle according to claim 1 wherein at least one peptide is linked to a drug.

7. A peptidic nanoparticle according to claim 1 wherein at least one peptide is linked to an antigen.

8. A peptidic nanoparticle according to claim 1 wherein at least one peptide is non-covalently linked to a targeting entity, drug or antigen.

9. A pharmaceutical composition comprising a peptidic nanoparticle according to claim 1.

10. A peptidic nanoparticle according to claim 1 wherein m or n is 4.

11. A method for determining whether a human has diseased organs or tissues comprising:
administering an effective amount of a functionalized peptidic nanoparticle according to claim 1 which is substituted with a drug that is a diagnostic molecule.

* * * * *